United States Patent [19]

Gozzo et al.

[11] 4,008,071
[45] Feb. 15, 1977

[54] ADDUCTS OF CARBAMOYL SULPHOXIDES

[75] Inventors: Franco Gozzo, S. Donato Milanese (Milan); Marcella Masoero, Milan; Ernesto Signorini, Malnate (Varese); Riccardo Fabbrini, Milan, all of Italy

[73] Assignee: Montedison Fibre S.p.A., Milan, Italy

[22] Filed: Aug. 29, 1975

[21] Appl. No.: 608,976

Related U.S. Application Data

[63] Continuation-in-part of Ser. No. 584,352, June 6, 1975, Pat. No. 3,975,180.

[30] Foreign Application Priority Data

Sept. 3, 1974    Italy .................. 26861/74

[52] U.S. Cl. .................. 71/99; 71/98; 71/100; 71/103; 260/551 C; 260/551 S; 260/552 R; 260/553 R; 260/553 A; 260/553 E

[51] Int. Cl.² .................. A01N 9/14

[58] Field of Search .......... 71/99, 103, 98, 100; 260/551 R

[56] References Cited

UNITED STATES PATENTS

| | | | |
|---|---|---|---|
| 3,594,362 | 7/1971 | Szabo | 71/99 |
| 3,816,435 | 6/1974 | Walker | 71/94 |
| 3,816,436 | 6/1974 | Walker | 71/94 |
| 3,816,502 | 6/1974 | Pallos et al. | 260/455 A |
| 3,862,976 | 1/1975 | Booth | 260/455 A X |
| 3,879,455 | 4/1975 | Tilles | 71/103 |
| 3,896,169 | 7/1975 | Tilles | 260/551 R |
| 3,910,935 | 10/1975 | Walker | 71/94 |

*Primary Examiner*—Joseph Paul Brust
*Attorney, Agent, or Firm*—Stevens, Davis, Miller & Mosher

[57] ABSTRACT

Novel adducts of a carbamoyl sulphoxide and urea having the formula

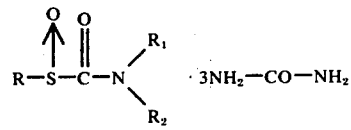

and adducts of the said carbamoyl sulphoxide and an organic compound having the grouping

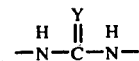

wherein R is substituted or unsubstituted aryl, alkyl or alkenyl; $R_1$ and $R_2$, which may be the same or different, are H, substituted or unsubstituted alkyls, alkenyls or aryls, or aliphatic groups that, bound to one another in the form of a chain $-(CH_2)_p-(X)_n-(CH_2)_q-$ (in which $p = 1,2,3$; $q = 1,2,3$; X is O, S, SO, $SO_2$; $n = 0$ or 1), form with N a ring when $n = 1$ and $(p+q) \leq 4$, and y is O, S or N- are contemplated. The adducts have herbicidal properties and herbicide compositions containing the adducts as well as a process for inhibiting the growth of plants or for destroying them with a herbicide containing the adduct are also contemplated.

6 Claims, No Drawings

ADDUCTS OF CARBAMOYL SULPHOXIDES

This application is a continuation-in-part of our application Ser. No. 584,352, now U.S. Pat. No. 3,975,180, issued Aug. 17, 1976, filed June 6, 1975.

This invention relates to adducts of carbamoyl sulphoxides and urea, thiourea and derivatives of urea which are stable, crystalline adducts having interesting, long-lasting herbicidal properties. More particularly, this invention relates to the adducts, the method of preparing them and compositions containing them.

A prior patent application filed on Oct. 5, 1973, U.S. Ser. No. 403,820 assigned to the assignee of this application describes carbamoyl sulphoxides having the general formula:

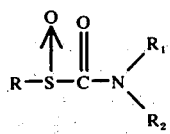

wherein R is aryl, alkyl or alkenyl which may be unsubstituted or substituted; $R_1$ and $R_2$, which may be the same or different, are H, alkyl, alkenyl or aryl, which may be unsubstituted or substituted, or aliphatic groups that, bound to one another in the form of a chain $-(CH_2)_p - (X)_n -(CH_2)_q -$ (in which $p = 1,2,3$; $q = 1,2,3$; $X = > O; > S; > SO$ or $> SO_2$ and $n = O$ or 1), form with N-when $n = 1$ and $(p+q) \leq 4$ - a ring. Such carbamoyl sulphoxides exert an interesting herbicidal action towards both monocotyledons and infesting latifoliae, while they are innocuous towards important agrarian cultures.

It is an object of the present invention to provide a new class of crystalline adducts of carbamoyl sulphoxides and urea, mono-substituted urea, a biuret, thiourea, dicyanodiamide, dichloralurea, and the like which have good thermal stability and retain at least the herbicidal activity typical of the carbamoyl sulphoxides.

Another object of this invention is to provide adducts having herbicidal properties which are capable of gradually and regularly releasing the active substance, once they are applied to the soil.

A further object of the invention is to provide herbicides which are easy to formulate.

A still further object is to provide a method of preparing the adducts provided by the invention.

As set forth in our earlier application, these objects and others are achieved by providing adducts of carbamoyl sulphoxides and urea having the general formula:

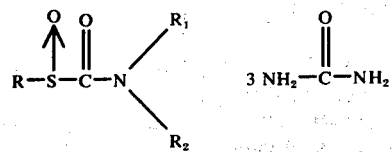 (I)

wherein R is an aryl, alkyl or alkenyl radical, optionally substituted; $R_1$ and $R_2$ may be the same or different and are H, alkyls, alkenyls or aryls which may or may not be substituted, or aliphatic groups that, bound to one another in the form of a chain $-(CH_2)_p-(X)_n-(CH_2)_q-$ (in which $p = 1,2,3$; $q = 1,2,3$; X is $=O$; $=S$; $=SO$ or $=SO_2$ and $n = O$ or 1), form with N — when $n = 1$ and $(p + q) \leq 4$ — a ring. Such adducts are solid and crystalline. They exhibit, on infrared spectrophotometric analysis, a shifting of the frequencies relevant to the vibrations of bonds N—H, N—C—N and S—O with respect to the corresponding ones of the urea and of the starting carbamoyl sulphoxides. On X-ray analysis, they exhibit spectral lines different from those typical of urea and of the starting carbamoyl sulphoxides if the latter are in the solid state and their centesimal composition is in accordance with formula (I).

It has now been found that the carbamoyl sulphoxides having the formula

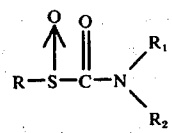

(in which R, $R_1$ and $R_2$ have the same meanings as specified hereinbefore) form adducts with organic compounds containing in their structure the following group:

in which Y = O; S; N-.

Organic compounds containing a group of that type are monosubstituted ureas such as, for example, phenylurea, biuret, thiourea, dicyanodiamide, dichloralurea, and the like.

Hence, the invention contemplates broadly adducts prepared by reacting carbamoyl sulphoxides having the formula:

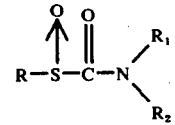

wherein R is substituted or unsubstituted aryl, alkyl or alkenyl; $R_1$ and $R_2$, which may be the same or different, are H, substituted or unsubstituted alkyls, alkenyls or aryls, or aliphatic groups that, bound to one another in the form of a chain $-(CH_2)_p-(X)_n-(CH_2)_q-$ (in which $p = 1,2,3$; $q = 1,2,3$; $X =, =O, =S; =SO, =SO_2$; $n = O$ or 1), form with N a ring when $n = 1$ and $(p+q) \leq 4$ with a compound containing the grouping $H_m$-(NH-CY-NH)-(H)_m$ where $m$ is O or 1 and Y is O; S or N—.

The following Table 1 lists examples of some adducts of carbamoyl sulphoxides and urea falling under the general formula of the present invention, near which the infrared frequencies characteristic of the most meaningful bonds are indicated by way of comparison with the frequencies relating to urea. The shifting of the main band due to bond S → O is reported as the difference — in $cm^{-1}$ — between the frequency of the most intense band due to such grouping in the adduct and the frequency of the main band of group S O in the starting carbamoyl sulphoxide ($\Delta\gamma$).

TABLE 1

Infrared frequency of adducts having general formula I as compared with those of the components.

| ADDUCT | | FREQUENCY OF BONDS (cm$^{-1}$) | | $\Delta\nu$ (cm$^{-1}$) of group S→O with respect to each carbamoyl sulphoxide |
|---|---|---|---|---|
| Item No. | R | R$_1$ = R$_2$ | N—C—N | N—H | |
| 5675 U | CH$_3$ | iso C$_4$H$_9$ | 799 | 3378 – 3185 | – 8 |
| 5105 U | C$_2$H$_5$ | n. C$_3$H$_7$ | 797 | 3367 – 3185 | – 5 |
| 5286 U | C$_2$H$_5$ | iso C$_4$H$_9$ | 797 | 3390 – 3195 | – 2 |
| 5197 U | n.C$_3$H$_7$ | n. C$_3$H$_7$ | 799 | 3378 – 3185 | – 6 |
| 5451 U | n.C$_3$H$_7$ | i. C$_4$H$_9$ | 796 | 3390 – 3185 | –16 |
| 5193 U | iso C$_3$H$_7$ | n. C$_3$H$_7$ | 800 | 3370 – 3185 | ⎧–22 |
| 5452 U | iso C$_3$H$_7$ | iso C$_4$H$_9$ | 795 | 3390 – 3185 | ⎨– 4 |
| | | | | | ⎩– 2 |
| 5517 U | iso C$_4$H$_9$ | iso C$_4$H$_9$ | 795 | 3390 – 3185 | – 9 |
| 5104 U | C$_6$H$_5$CH$_2$ | n. C$_3$H$_7$ | 797 | 3356 – 3185 | – 3 |
| | UREA | | 787 | 3250 – 3355 | — |

The adducts of this invention, unlike the most interesting terms of the carbamoyl sulphoxides series, are stable in storage and can be indefinitely preserved at room temperature.

For purposes of comparison with the thermal stability of the carbamoyl sulphoxides as such, Table 2 reports the percentages of carbamoyl sulphoxide recovered from the corresponding adduct after residence at temperatures higher than room temperature, along with the percentages of same recovered after conditioning of carbamoyl sulphoxide as such at 50° and 100° C.

The recovery of carbamoyl sulphoxide from the adduct at the conclusion of the conditioning period is carried out by extraction with chloroform: the dose of carbamoyl sulphoxide in the extracts is determined by chromatography on a thin layer or by gas-chromatography according to conventional techniques.

lines of the Debye-diagram are different from those of the starting compounds.

Since the adduct can be easily crystallized and the carbamoyl sulphoxide is easily recoverable from same by mild hydrolysis and/or extraction with chloroform or another proper solvent, it is evident that the adduct formation may be utilized to purify the carbamoyl sulphoxide.

It is to be pointed out that the molar ratios of carbamoyl sulphoxide to the organic compound containing group

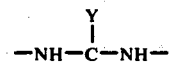

vary, in the adducts of this invention, depending upon

TABLE II

Percentages of carbamoyl sulphoxide recovered from the adduct after 14 days at 54° C and after 8 hrs. at 100° C in comparison with the carbamoyl sulphoxide present after treatment at 50° C for 13 days and at 100° C for 8 hrs.

| | ADDUCT | | % OF CARBAMOYL SULPHOXIDE RECOVERED | | | |
|---|---|---|---|---|---|---|
| | | | FROM CARBAMOYL SULPHOXIDE | | FROM THE ADDUCT | |
| Item No. | R | R$_1$ = R$_2$ | 50° C; 13 days | 100° C; 8 hrs. | 54° C; 14 days | 100° C; 8 hrs. |
| 5105 U | C$_2$H$_5$ | n. C$_3$H$_7$ | 87 | ~51 | 90 | 75 |
| 5197 U | n. C$_3$H$_7$ | n. C$_3$H$_7$ | 74 | ~ 0 | 87 | 63 |
| 5451 U | n. C$_3$H$_7$ | iso C$_4$H$_9$ | 75 | ~ 0 | 95 | 80 |
| 5193 U | iso C$_3$H$_7$ | n. C$_3$H$_7$ | 24 | ~ 0 | 96 | 91 |
| 5452 U | iso C$_3$H$_7$ | iso C$_4$H$_9$ | 50 | ~ 0 | 96 | 89 |

The adducts corresponding to formula I may be obtained through a very simple process, which is also an object of this invention and consists in adding the carbamoyl sulphoxide to a solution of urea in a suitable solvent, and in concentrating such mixture. The adduct precipitates and is then collected and dried. The adduct of carbamoyl sulphoxide and an organic compound having the grouping —NH—CY—NH— may be prepared by the same method as the adduct of formula I with appropriate substitution of the compound having the said grouping for urea.

When the carbamoyl sulphoxide : urea molar ratios are = 1:3, the solvent may be also evaporated to dryness.

The formation and composition of the adduct corresponding to formula I are proved by the fact that, even if the carbamoyl sulphoxide is mixed with a urea solution in molar ratios other than 1:3, the precipitate obtained by concentration always consists in a white crystalline solid, wherein the molar ratios are those indicated by formula I and wherein the frequencies of the bands characteristic of the spectrum and the spectral the nature of the organic compound. It is necessary, however, to ascertain each time which is the molar ratio of each individual adduct obtained, utilizing, to this aim, fractional crystallization followed by infrared spectrophotometric analysis, by elemental analysis and, optionally, by X-ray diffractometric analysis of the precipitate that has formed. After having ascertained which is the molar ratio at which the desired adduct forms, the carbamoyl sulphoxide may be reacted with the stoichiometric amount of the compound containing the grouping —NH—CY—NH— necessary to provide the desired adduct and the solvent removed by evaporation.

Most of the adducts so prepared are crystalline solids, stable at room temperature and not subject to alteration during storage. Unlike carbamoyl sulphoxide, from which they are obtained, some of these adducts may be subjected to even long-lasting heat treatments at temperatures around 50° C without undergoing substantial modifications.

The shifting of the frequencies relating to the vibrations of bonds NH, N—C—N and S → O with respect to those of the corresponding starting products reveals whether the adduct has formed, as it will clearly appear from the following examples 5 through 9.

The herbicidal activity of the adducts provided by this invention is no lower than the activity of the corresponding carbamoyl sulphoxide as such when the doses applied to the soil, calculated as carbamoyl sulphoxide content, are equal.

The following examples are given better to illustrate the present industrial invention.

EXAMPLE 1

Preparation of

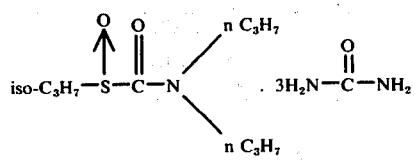

(5193 - U) from carbamoyl sulphoxide and urea in a 1 : 3 molar ratio. 3 g of isopropyl-N-di-n-propylcarbamoyl sulphoxide were added to 13.84 g of a methanol solution containing 2.48 g of urea. By slow evaporation under vacuum at room temperature the following four precipitate fractions were successively isolated which, after drying, were weighed and subjected to elemental analysis, the results thus obtained being reported in the following Table III.

TABLE III

| Fraction | Adduct Weight, g | Elemental Analysis | | | |
| --- | --- | --- | --- | --- | --- |
| | | C% | H% | N% | S% |
| I | 1.905 | 38.56 | 8.30 | 24.78 | 8.06 |
| II | 1.658 | 38.63 | 8.23 | 24.75 | 7.94 |
| III | 0.260 | 39.05 | 8.31 | 24.82 | 7.76 |
| IV | 0.770 | 38.05 | 8.16 | 25.07 | 7.40 |
| Theoretical Analysis: | | 39.08 | 8.32 | 24.54 | 8.02 |

All of the four fractions thus obtained, when subjected to X-ray analysis, produced Debye-diagrams containing the same spectral lines, sharply differentiated from those typical of urea.

The infrared spectra of the fractions were also like one another and contained the absorption bands shown in Table I.

EXAMPLE 2

Preparation of 5193 - U starting from carbamoyl sulphoxide and urea in molar ratios different from 1 : 3. 0.505 g of isopropyl-N-di-n-propylcarbamoyl sulphoxide was added to 0.760 g of a methanol solution containing 0.136 g of urea (initial molar ratio of the reagents in the order indicated : 1:0.98). After having allowed the solution to stand, a precipitate was collected that, after drying, weighed 0.202 g, and from whose elemental analysis the following results were obtained:

| C% | H% | N% | S% |
| --- | --- | --- | --- |
| 39.52 | 8.54 | 24.63 | 7.47 |

The infrared spectrum and the Debye-diagram of this precipitate are like the corresponding spectra relative to the precipitates obtained in Example 1.

Thoroughly similar results were obtained starting from the following starting amounts of reagents:
0.268 g of isopropyl-N-di-n-propylcarbamoyl sulphoxide;
1.921 g of a methanol solution containing 0.344 g of urea (initial molar ratio between the two reagents = 1 : 4.68).

EXAMPLE 3

By operating according to the method described in Example 1, the compounds reported on Table I were prepared, whose adduct nature is proved by the most meaningful I.R. frequencies reported on aforesaid table. Individual samples of these adducts resulted in a correct elemental analysis.

Similar results were obtained by employing, during preparation, a urea-saturated aqueous solution.

EXAMPLE 4

Herbicide Activity Tests

Adduct M 5193 - U, prepared according to the method of Example 1, by collecting all the fractions until thorough evaporation of the solvent, was divided into two equal samples.

One of these samples was further treated according to known formulation techniques, thus obtaining a cellulose powder containing the 2% of adduct (Sample 2).

On both the adduct (Sample 1) and the solid formulate (Sample 2), herbicidal activity tests were carried out in comparison with the corresponding carbamoyl sulphoxide as such.

Sample 1 was dissolved in a hydroacetone solution at 25% by volume of acetone. This solution was sprayed onto the earth contained in boxes measuring 40 × 30 × 20 cm, in whose upper part, a 5 cm thick layer, the seeds of the following infesting weeds had been uniformly distributed:

| monocotyledons: | Echinochloa crus galli |
| --- | --- |
| | Avena fatua |
| | Lolium sp. |
| | Sorghum sp. |
| | Setaria glauca |
| dicotyledons: | Stellaria media |
| | Ipomea sp. |
| | Vigna Sinensis |
| | Rumex Crispus |
| | Galinsoga sp. |

The 5 cm layer wherein these seeds were distributed had been laid onto a previously humidified soil. Under thoroughly identical conditions, as many boxes were prepared by spraying sample 2 (prepared in powder at the indicated titra, on a cellulose support) onto the surface and, for comparative purposes, a third set of as many likewise prepared boxes, onto which a hydroacetone solution of the carbamoyl sulphoxide as such was sprayed.

The process was repeated on further three sets of boxes, into which the preparations were incorporated by hoeing the first 5 cm of the upper layer.

The doses of each preparation were selected so as to apply to the soil amounts equal to 0.250; 0.500; 1 and 2 kg/ha respectively, calculated as carbamoyl sulphoxide.

After a 28-day residence in a glasshouse (temperature: 15° to 22° C. and regular daily irrigations), the results obtained are those reported in the following Table IV, using the activity indexes indicated hereinbelow:

| | | |
|---|---|---|
| 0 | = | no activity |
| 1; 2 | = | insufficient activity |
| 3 | = | high activity |
| 4 | = | total activity. |

By evaporation of the solvent a crystalline solid was obtained, that exhibited the following characteristics:

Melting point = 101 to 102° C
C%: calculated = 57.90    found = 57.45
H%: calculated = 8.22     found = 8.33
H%: calculated = 11.82    found = 11.82
S%: calculated = 9.02     found = 9.00

TABLE IV

Herbicide Activity in a glasshouse of adduct 5193 U according to the invention as compared with that of the corresponding carbamoyl sulphoxide

| | Dose kg/ha of carbamoyl sulphoxide | Application by incorporation | | | | | | | | | |
|---|---|---|---|---|---|---|---|---|---|---|---|
| | | MONOCOT. | | | | | DICOT. | | | | |
| Applied Product | | ECHINO-CHLOA | AVENA FATUA | LOL-IUM | SOR-GHUM | SET-ARIA | STELL-ARIA | IPO-MEA | VIG-NA | RUMEX | GALIN-SOGA |
| Hydroacetone solution of adduct 5913 — Urea. | 0.25 | 3 | 3 | 4 | 4 | 4 | 3 | 1 | 2 | 0 | 0 |
| | 0.50 | 4 | 3 | 4 | 4 | 4 | 4 | 2 | 3 | 1 | 1 |
| | 1.00 | 4 | 4 | 4 | 4 | 4 | 4 | 3 | 4 | 3 | 3 |
| | 2.00 | 4 | 4 | 4 | 4 | 4 | 4 | 4 | 4 | 4 | 4 |
| Powder containing 2% of adduct — Urea on cellulose support. | 0.25 | 3 | 3 | 4 | 4 | 4 | 2 | 0 | 2 | 0 | 0 |
| | 0.50 | 4 | 3 | 4 | 4 | 4 | 4 | 1 | 3 | 1 | 1 |
| | 1.00 | 4 | 4 | 4 | 4 | 4 | 4 | 3 | 4 | 3 | 3 |
| | 2.00 | 4 | 4 | 4 | 4 | 4 | 4 | 4 | 4 | 4 | 4 |
| Carbamoyl sulphoxide 5193 as such. | 0.25 | 3 | 1 | 4 | 4 | 4 | 2 | 0 | 1 | 0 | 0 |
| | 0.50 | 4 | 3 | 4 | 4 | 4 | 3 | 1 | 3 | 0 | 0 |
| | 1.00 | 4 | 4 | 4 | 4 | 4 | 4 | 2 | 3 | 1 | 1 |
| | 2.00 | 4 | 4 | 4 | 4 | 4 | 4 | 4 | 4 | 4 | 4 |

| | Dose kg/ha of carbamoyl sulphoxide | Surface application | | | | | | | | | |
|---|---|---|---|---|---|---|---|---|---|---|---|
| | | MONOCOT. | | | | | DICOT. | | | | |
| Applied Product | | ECHINO-CHLOA | AVENA FATUA | LOL-IUM | SOR-GHUM | SET-ARIA | STELL-ARIA | IPO-MEA | VIG-NA | RUMEX | GALIN-SOGA |
| Hydroacetone solution of adduct 5193 — Urea. | 0.25 | 3 | 2 | 3 | 3 | 3 | 3 | 0 | 2 | 0 | 0 |
| | 0.50 | 4 | 3 | 4 | 4 | 4 | 3 | 1 | 3 | 1 | 1 |
| | 1.00 | 4 | 4 | 4 | 4 | 4 | 4 | 3 | 4 | 3 | 3 |
| | 2.00 | 4 | 4 | 4 | 4 | 4 | 4 | 4 | 4 | 4 | 4 |
| Powder containing 2% of adduct — Urea on cellulose support. | 0.25 | 3 | 2 | 3 | 2 | 2 | 2 | 0 | 2 | 0 | 0 |
| | 0.50 | 4 | 3 | 4 | 4 | 4 | 3 | 1 | 2 | 0 | 1 |
| | 1.00 | 4 | 4 | 4 | 4 | 4 | 4 | 3 | 4 | 2 | 2 |
| | 2.00 | 4 | 4 | 4 | 4 | 4 | 4 | 3 | 4 | 4 | 4 |
| Carbamoyl sulphoxide 5193 as such. | 0.25 | 3 | 0 | 1 | 0 | 1 | 3 | 2 | 2 | 0 | 0 |
| | 0.50 | 4 | 2 | 2 | 1 | 2 | 4 | 4 | 4 | 0 | 0 |
| | 1.00 | 4 | 2 | 4 | 4 | 4 | 4 | 2 | 3 | 1 | 2 |
| | 2.00 | 4 | 4 | 4 | 4 | 4 | 4 | 3 | 4 | 2 | 2 |

EXAMPLE 5

Preparation and characteristics of the adduct:

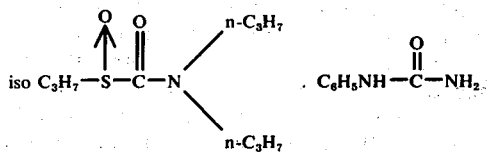 . $C_6H_5NH-\overset{\overset{O}{\|}}{C}-NH_2$

Carbamoyl sulphoxide was added to a solution of phenylurea in methanol. After evaporation, a number of fractions were obtained, out of which only one revealed, on elemental analysis and infrared spectrophotometric analysis, to be an adduct having a molar ratio of carbamoyl sulphoxide to phenylurea of 1 : 1.

The preparation was repeated adding 0.1 mole of sulphoxide in a methanol solution containing 0.1 mole of urea.

The frequencies in cm$^{-1}$ of the bands of the adduct infrared spectrum as compared with those of carbamoyl sulphoxide and of phenylurea are reported on following Table V.

TABLE V

| | Zone $\nu$ (NH) | Zone $\nu$ (S→O) | Zone $\nu$ (N—C—N) |
|---|---|---|---|
| Carbamoyl sulphoxide | | 1064 1028 | |
| Phenylurea | 3425 3311 3205 | | 752 |
| Adduct of example 5 | 3373 3195 | 1063 1030 | 760 |

A sample of the adduct was kept in a closed tube (in the presence of air) at a temperature of 54° C for 14 days. At the end of this time-period, it was extracted with chloroform and subjected to analysis on a thin layer: it resulted that the carbamoyl sulphoxide which remained unchanged amounted to about 90% of the carbamoyl sulphoxide initially present in the adduct.

EXAMPLE 6

Characteristics of the adduct :

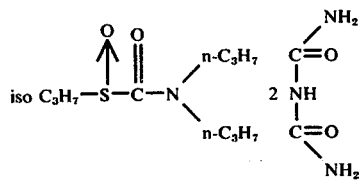

Following the method previously described, it was ascertained that the adduct obtained had the composition reported hereinbefore. Thus, a certain amount of same was prepared by adding 0.1 moles of carbamoyl sulphoxide to 0.2 moles of biuret in methanol. After removal of the solvent, the crystalline product exhibited the following elemental analysis :

| Elemental analysis: | C% | | H% | | N% | | S% | |
|---|---|---|---|---|---|---|---|---|
| | calc. | found | calc. | found | calc. | found | calc. | found |
| Adduct 2:3 | 41.41 | 40.90 | 8.16 | 8.18 | 16.80 | 16.86 | 24.03 | 23.71 |
| Adduct 1:2 | 39.10 | 39.76 | 7.87 | 8.07 | 18.85 | 18.35 | 25.88 | 24.00 |

C%: calc. = 39.51  found = 39.01
H%: calc. = 7.34   found = 7.31
H%: calc. = 23.04  found = 22.94
S%: calc. = 7.53   found = 7.53

The product thus obtained had a melting point > 104° C. Frequencies γ in cm$^{-1}$ of the bands of the adduct I.R.-spectrum as compared with those of carbamoyl sulphoxide and of biuret are reported on following Table VI.

TABLE VI

| | Zone | Zone | Zone |
|---|---|---|---|
| | ν(NH) | ν(S→O) | ν(N—C—N) |
| Sulphoxide | | 1064 | |
| | | 1028 | |
| Biuret | 3484 | | 763 |
| | 3401 | | 711 |
| | 3185 | | |
| Adduct of example 6 | 3356 | 1058 | 783 |
| | 3175 | 1030 | 716 |

This adduct was subjected to thermal conditioning at a temperature of 54° C for 14 days, according to the modalities described in example 5. The results of the analyses carried out on such adduct revealed that about 85% of the carbamoyl sulphoxide initially contained in the adduct had remained unchanged.

EXAMPLE 7

Characteristics of the adducts :

$$2 \text{ iso-C}_3\text{H}_7-\overset{O}{\overset{\uparrow}{S}}-\overset{O}{\overset{\|}{C}}-N\begin{matrix}n\text{-C}_3\text{H}_7 \\ n\text{-C}_3\text{H}_7\end{matrix} \cdot 3\ C\begin{matrix}NH_2 \\ \| \\ S \\ \backslash \\ NH_2\end{matrix}$$

and $$\text{iso-C}_3\text{H}_7-\overset{O}{\overset{\uparrow}{S}}-\overset{O}{\overset{\|}{C}}-N\begin{matrix}n\text{-C}_3\text{H}_7 \\ n\text{-C}_3\text{H}_7\end{matrix} \cdot 2\ C\begin{matrix}NH_2 \\ \| \\ S \\ \backslash \\ NH_2\end{matrix}$$

By operating according to the method previously illustrated, the two additives having the composition reported hereinabove were isolated and prepared. Also an adduct having a 1:2 molar ratio was isolated in an impure form.

Frequencies γ in cm$^{-1}$ of the bands of the I.R.-spectra of the adducts and of the starting products are reported on Table VII.

TABLE VII

| | Zone | Zone | Zone |
|---|---|---|---|
| | ν(NH) | ν(S→O) | ν(N—C—H) |
| Carbamoyl sulphoxide | | 1064 | |
| | | 1028 | |
| Thiourea | 3378 | | 730 |
| | 3279 | | |
| | 3175 | | |
| Adduct 2:3 | 3289 | 1059 | 731 |
| | 3165 | 1027 | |
| Adduct 1:2 | 3289 | 1059 | (735) |
| | 3165 | 1027 | 725 |

The adducts containing thiourea are not so stable, at 54° C, as those containing urea: in fact, after a 14-day conditioning at such temperature, about 12% of the initial carbamoyl sulphoxide were recovered from adduct 2:3 and about 20% of the initial carbamoyl sulphoxide were recovered from adduct 1:2.

EXAMPLES 8 AND 9

Characteristics of the adducts prepared from isopropyl N-di-n-propyl carbamoyl sulphoxide and dicyanodiamide, and from isopropyl N-di-n-propyl carbamoyl sulphoxide and dichloralurea :

$$\text{iso C}_3\text{H}_7-\overset{O}{\overset{\uparrow}{S}}-\overset{O}{\overset{\|}{C}}-N\begin{matrix}n\text{-C}_3\text{H}_7 \\ n\text{-C}_3\text{H}_7\end{matrix} \cdot H_2N-\overset{NH}{\overset{\|}{C}}-NH-C=N$$

m.p. = 67–68° C and

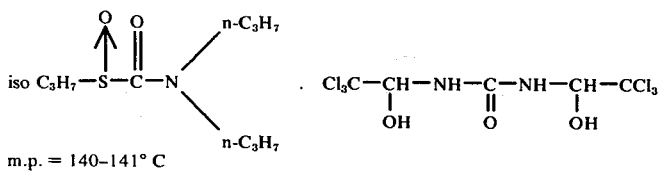

m.p. = 140–141° C

| Elemental analysis | C% calc. | found | H% calc. | found | N% calc. | found | S% calc. | found |
|---|---|---|---|---|---|---|---|---|
| Adduct with dicyanodiamide | 47,49 | 47,05 | 8,30 | 8,34 | 23,08 | 22,07 | 10,56 | 10,36 |
| Adduct with dichloralurea | 31,38 | 31,96 | 4,74 | 4,84 | 7,32 | 7,21 | 5,58 | 5,58 |

Frequency $\gamma$ in cm$^{-1}$ of the bands of the infrared spectra of the adducts and of the starting products is reported on following Table VIII.

TABLE VIII

| | Zone $\nu$ (N11) | Zone $\nu$ (S→O) | Zone $\nu$ (N—C—N) |
|---|---|---|---|
| Carbamoyl sulphoxide | | 1064 1028 | |
| Dicyanodiamide | 3448 3378 3333 3185 3145 | | 719 |
| Dichloralurea | 3279 | 1073 | (838) 824 (811) |
| Adduct with dicyanodiamide | 3356 3145 | 1064 1032 | 750 706 |
| Adduct with dichloralurea | 3289 3268 3185 | 1085 1055 1028 | (837) 815 806 |

The herbicide activity of the adducts prepared from compounds containing the grouping —NH—CY—NH—, with the doses given to the soil, calculated as carbamoyl sulphoxide content, being equal, was no lower than that of the corresponding carbamoyl sulphoxide as such and of the adducts prepared from carbamoyl sulphoxide and urea.

The herbicide activity was tested on the following infesting weeds:

| monocotyledons: | Echinochloa crus-galli Avena fatua Lolium sp. Sorghum sp. Setaria glauca |
|---|---|
| dicotyledons: | Stellaria media Iponea sp. Vigna sinensis Rumex crispus Galinsoga sp. | under the same conditions illustrated in example 4 above. The results were substantially identical with those yielded by the adducts prepared from carbamoyl sulphoxides and urea.

Preferred adducts prepared by reacting a carbamoyl sulphoxide with a compound having the grouping —NH—CY—NH— have the formulae:

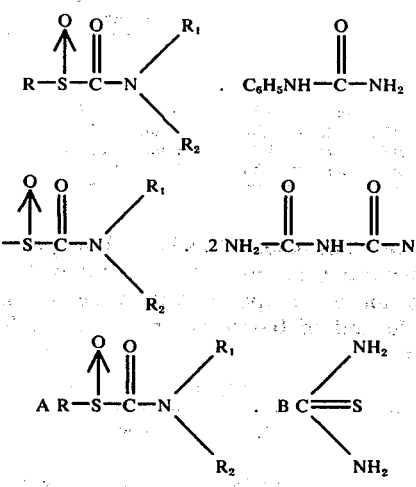

Although the invention has been described in detail for the purpose of illustration, it is to be understood that such detail is solely for that purpose and that variations can be made therein by those skilled in the art without departing from the spirit and scope of the invention except as it may be limited by the claims.

What we claim is:

1. A method for combating infesting plants by incorporating or spreading on the ground adjacent thereto in a quantity of at least 0.25 kg/ha, an adduct of
   a. one or two moles of a carbamoyl sulphoxide of the formula:

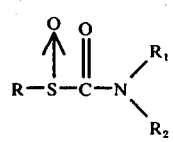

wherein R is a $C_1$ to $C_4$ alkyl group or a benzyl group, and $R_1$ and $R_2$ are each a $C_1$ to $C_4$ alkyl group, and b. one, two or three moles of a compound selected from the group consisting of phenylurea, biuret, thiourea, dicyanodiamide and dichloralurea.

2. A method as defined in claim 1, wherein the adduct has the formula:

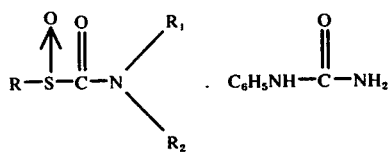

3. A method as defined in claim 1, wherein the adduct has the formula:

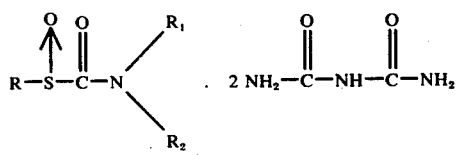

4. A method as defined in claim 1, wherein the adduct has the formula:

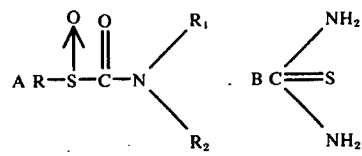

in which A is one or two and B is two or three.

5. A method as defined in claim 1, wherein the adduct has the formula:

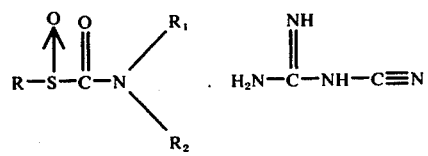

6. A method as defined in claim 1, wherein the adduct has the formula:

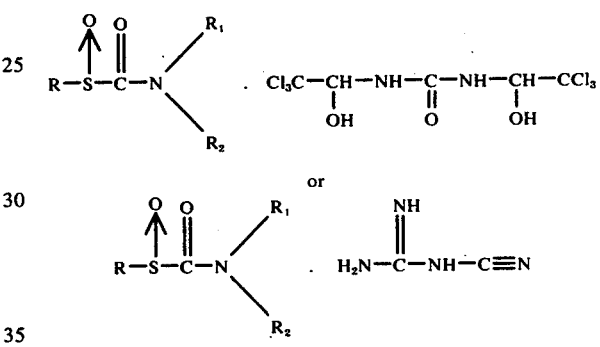

* * * * *

UNITED STATES PATENT OFFICE
CERTIFICATE OF CORRECTION

Patent No. 4,008,071     Dated February 15, 1977

Inventor(s) Franco GOZZO et al

It is certified that error appears in the above-identified patent and that said Letters Patent are hereby corrected as shown below:

At "[73] Assignee:" the word "Fibre" should be deleted, showing the correct assignee as
--Montedison S.p.A.--;

Under the heading "Foreign Application Priority Data", a second priority application should be added as follows:
--June 7, 1974   Italy...........23725/74--.

Signed and Sealed this fifth Day of July 1977

[SEAL]

Attest:

RUTH C. MASON
Attesting Officer

C. MARSHALL DANN
Commissioner of Patents and Trademarks